US011819434B2

(12) United States Patent
Osti et al.

(10) Patent No.: US 11,819,434 B2
(45) Date of Patent: Nov. 21, 2023

(54) JOINT STABILIZATION DEVICE, PARTICULARLY FOR THE PATELLOFEMORAL JOINT

(71) Applicants: Leonardo Osti, Modena (IT); Raffaella Osti, Ferrara (IT)

(72) Inventors: Leonardo Osti, Modena (IT); Raffaella Osti, Ferrara (IT)

(*) Notice: Subject to any disclaimer, the term of this patent is extended or adjusted under 35 U.S.C. 154(b) by 930 days.

(21) Appl. No.: 16/492,505

(22) PCT Filed: Mar. 9, 2018

(86) PCT No.: PCT/IB2018/051553
§ 371 (c)(1),
(2) Date: Sep. 9, 2019

(87) PCT Pub. No.: WO2018/163118
PCT Pub. Date: Sep. 13, 2018

(65) Prior Publication Data
US 2021/0128337 A1    May 6, 2021

(30) Foreign Application Priority Data
Mar. 10, 2017  (IT) .......................... 102017000027082

(51) Int. Cl.
  *A61F 5/01*      (2006.01)
  *A41D 1/06*      (2006.01)
  *A41D 27/00*     (2006.01)

(52) U.S. Cl.
  CPC .............. *A61F 5/0109* (2013.01); *A41D 1/06* (2013.01); *A41D 27/00* (2013.01); *A41D 2400/32* (2013.01)

(58) Field of Classification Search
  CPC ...... A61F 5/0109; A61F 5/0123; A61F 5/0125
  See application file for complete search history.

(56) References Cited

U.S. PATENT DOCUMENTS 4,296,744 A * 10/1981 Palumbo ............... A61F 13/062
                                                    2/24
5,024,216 A *  6/1991 Shiono ................. A61F 5/0123
                                                    2/24
(Continued)

FOREIGN PATENT DOCUMENTS

DE     20 2015 003 437 U1     7/2015

*Primary Examiner* — Camtu T Nguyen
(74) *Attorney, Agent, or Firm* — ASLAN LAW, P.C.

(57) ABSTRACT

A joint stabilization device including at least support means positionable at the patellar portion of a leg of a patient; a sustaining element of elongated shape, having a first extremity and a second extremity opposite to each other, associated with the support means and positionable laterally to the patella of the patient; a first traction element and a second traction element associated with the first extremity and with the second extremity, respectively; and a first directing element and a second directing element which are associated with the sustaining element and interposed between the first extremity and the first traction element and between the second extremity and the second traction element respectively, wherein the first traction element and the second traction element are adapted to position the sustaining element in a predefined position, the first directing element and the second directing element being adjustable depending on the predefined position.

18 Claims, 3 Drawing Sheets

(56) References Cited

U.S. PATENT DOCUMENTS

| | | | | |
|---|---|---|---|---|
| 5,277,697 A | * | 1/1994 | France | A61F 13/062 |
| | | | | 602/26 |
| 5,556,374 A | * | 9/1996 | Grace | A61F 5/0109 |
| | | | | 602/26 |
| 6,287,269 B1 | | 9/2001 | Osti | |
| 6,551,264 B1 | * | 4/2003 | Cawley | A61F 5/0125 |
| | | | | 128/882 |
| 7,819,830 B2 | * | 10/2010 | Sindel | A61F 5/0109 |
| | | | | 128/882 |
| 8,926,539 B2 | * | 1/2015 | Cropper | A61F 5/0123 |
| | | | | 602/26 |
| 2004/0054307 A1 | * | 3/2004 | Mason | A61F 5/0125 |
| | | | | 602/16 |
| 2009/0156973 A1 | * | 6/2009 | Scott | A61F 5/0106 |
| | | | | 602/26 |

\* cited by examiner

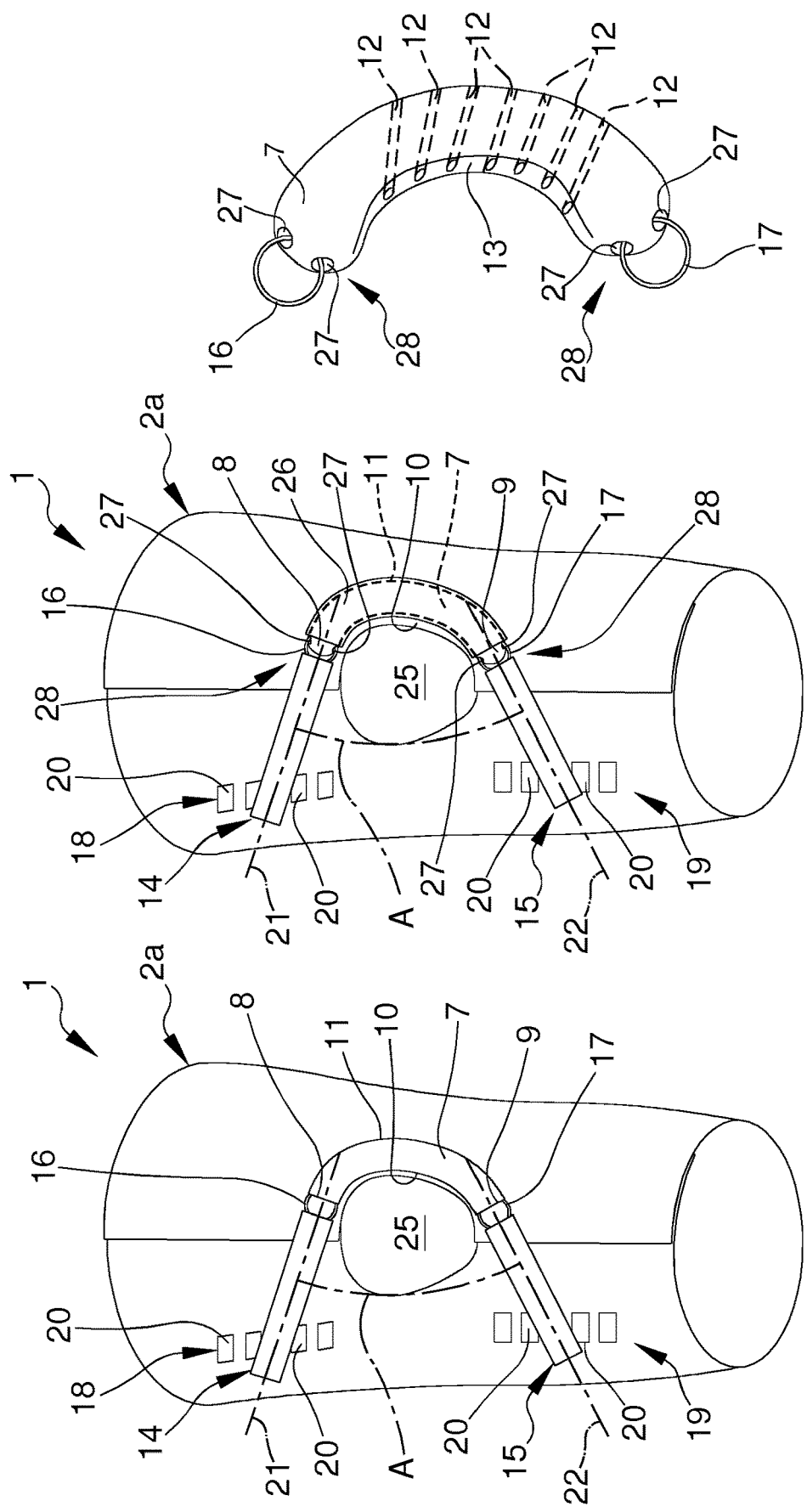

JOINT STABILIZATION DEVICE, PARTICULARLY FOR THE PATELLOFEMORAL JOINT

CROSS-REFERENCE TO RELATED APPLICATIONS

This application claims priority to IT Patent Application No. 102017000027082 filed on Mar. 10, 2017, and to PCT Application No. PCT/IB2018/051553 filed on Mar. 9, 2018, the entire contents of which are hereby incorporated by reference.

TECHNICAL FIELD

The present invention relates to a joint stabilization device, particularly for the patellofemoral joint.

BACKGROUND ART

With reference to the orthopedic sector, the use is known of joint stabilization devices, so-called knee pads, in order to give stability to the knee joints both during sports activities, such as e g running, and following surgery or traumatic lesions in which the healing process requires keeping the knee and its surrounding joints in a predefined position.

Generally speaking, known knee pads comprise a tubular element made of elastic material and wearable by a patient at the patellar portion.

The tubular element is generally provided with a front through hole which, in the wearing configuration, is adapted to accommodate at least part of the patient's patella, blocking it in the respective joint seat.

Nevertheless, this type of knee pad has many drawbacks, particularly related to the discomfort caused to the patient by the prolonged use of same.

In fact, the shape of the knee pad, besides being a cause of discomfort, causes muscular stress linked to the overheating of the underlying tissue wrapped in the tubular element and, at the same time, causes an increase in inflammatory conditions, considerably prolonging the healing times.

In order to avoid the aforementioned drawbacks, at least in part, a second type of knee pad has been developed, which comprises the tubular element and support means of reticular conformation associated with the latter, and positionable at the patellar portion.

The reticular conformation of the support means is adapted to allow the dispersion of energy and shock absorption in order to relieve the pain felt during muscle activity, in case of intense physical effort, as well as from inflammatory or post-operative conditions.

Nevertheless, even the above second type of knee pad has numerous drawbacks linked to the inconvenience of use of same and to the difficulty of moving the leg.

An alternative to this type of stabilization device is represented by the knee pad described in the U.S. Pat. No. 6,287,269.

This knee pad also has the tubular element and, furthermore, a patella sustaining element associated with the tubular element itself.

The sustaining element has an elongated substantially C-shaped conformation having the extremities associated with respective traction elements adapted to retain the patella in a predefined position.

The sustaining element can be positioned sideways to the patella in such a way as to surround it at least partly.

The traction elements are made of inextensible material and the traction force exerted by these on the patella is variable according to the fastening to the fastening means.

The fastening means comprise two portions of Velcro aligned the one with the other and arranged on a portion of the tubular element opposite with respect to the sustaining element.

The traction means are associable with the fastening means and, depending on the predefined position to be obtained, the traction exerted by the traction elements on the patella can be adjusted.

In other words, the position of the sustaining element is variable according to the traction exerted by the traction elements on the same.

Nevertheless, even this type of knee pad has a number of drawbacks linked to the force exerted on the patella which affects the surrounding muscles, thus causing an inhibitory effect on the adjacent joint.

To this must be added that the shape of the tubular element causes the overheating of the muscles surrounding the patella, increasing the inflammatory condition and prolonging recovery and healing times.

Other stabilization devices are described in the Patent Document no. DE202015003437.

DESCRIPTION OF THE INVENTION

The main aim of the present invention is to provide a joint stabilization device, particularly for the patellofemoral joint, which allows stimulating the muscles surrounding the patella from a neuromuscular point of view, considerably reducing recovery and healing times.

Another object of the present invention is to provide a joint stabilization device, particularly for the patellofemoral joint, which allows modulating the patella position to be obtained according to the patient's needs.

Another object of the present invention is to provide a joint stabilization device, particularly for the patellofemoral joint, which allows overcoming the aforementioned drawbacks of the prior art within the scope of a simple, rational, easy, efficient to use and cost-effective solution.

The aforementioned objects are achieved by the present joint stabilization device, particularly for the patellofemoral joint, having the characteristics of claim 1.

BRIEF DESCRIPTION OF THE DRAWINGS

Other characteristics and advantages of the present invention will become more evident from the description of a preferred, but not exclusive embodiment of a joint stabilization device, particularly for the patellofemoral joint, illustrated by way of an indicative, but non-limiting example, in the attached drawings in which:

FIG. 3 is a front view of the stabilization device according to the invention in a second embodiment;

FIG. 4 is a front view of the device according to the invention in a third embodiment;

FIG. 5 is a view of a detail of a part of FIG. 3;

EMBODIMENTS OF THE INVENTION

Figure 2:
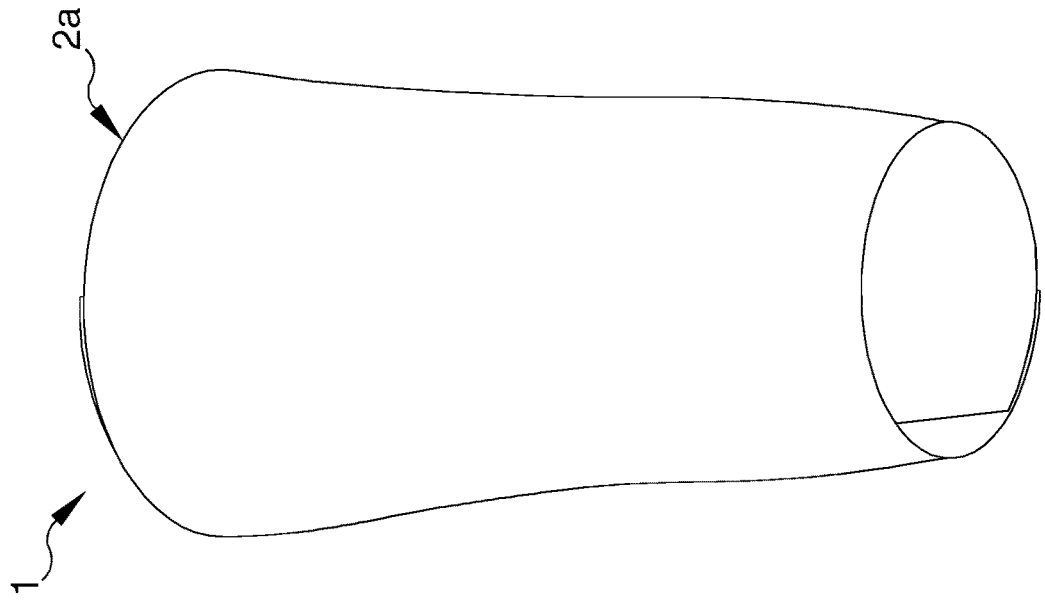
FIG. 2 is a rear view of the stabilization device of FIG. 1.

With particular reference to these illustrations, reference numeral 1 globally indicates a joint stabilization device, particularly for the patellofemoral joint.

The device 1 comprises support means 2a, 2b positionable at the patellar portion 3 of a leg 4 of a patient 5.

The support means 2a, 2b comprise a band element 2a enveloping around the patellar portion 3.

The band element 2a is re-closable to wrap the knee 6 by interposition of closing means, not shown in detail in the figures.

Figure 1:
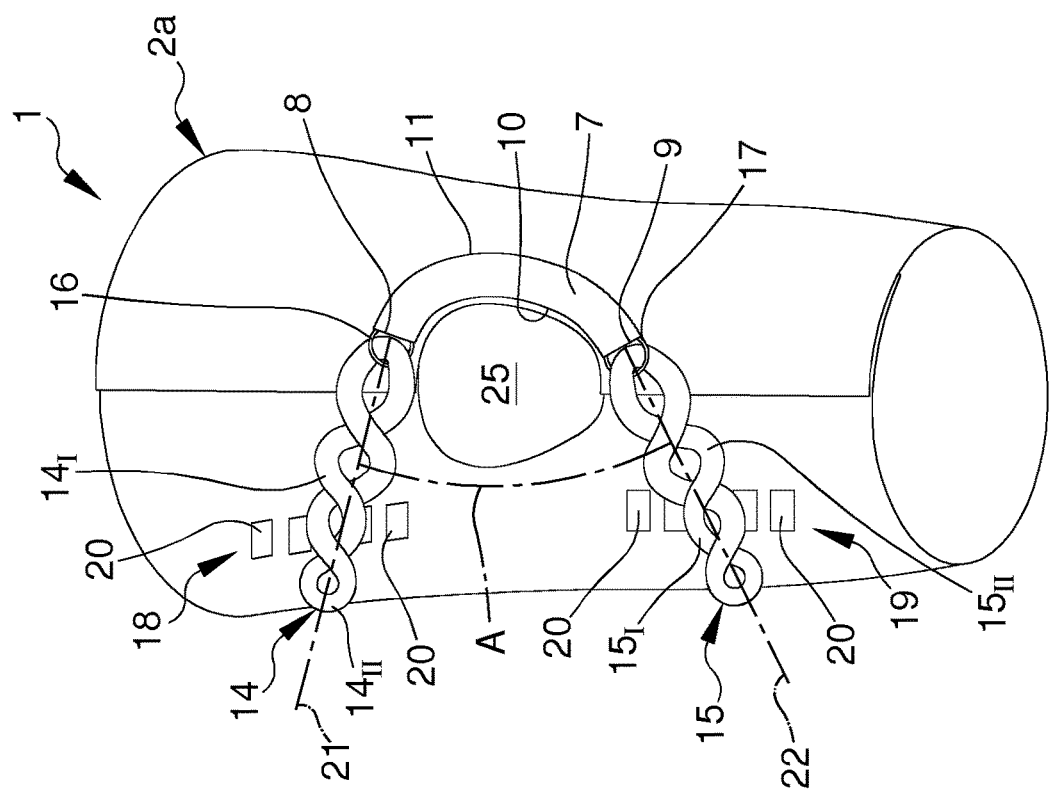
FIG. 1 is a front view of the stabilization device according to the invention in a first embodiment.
Figure 6:
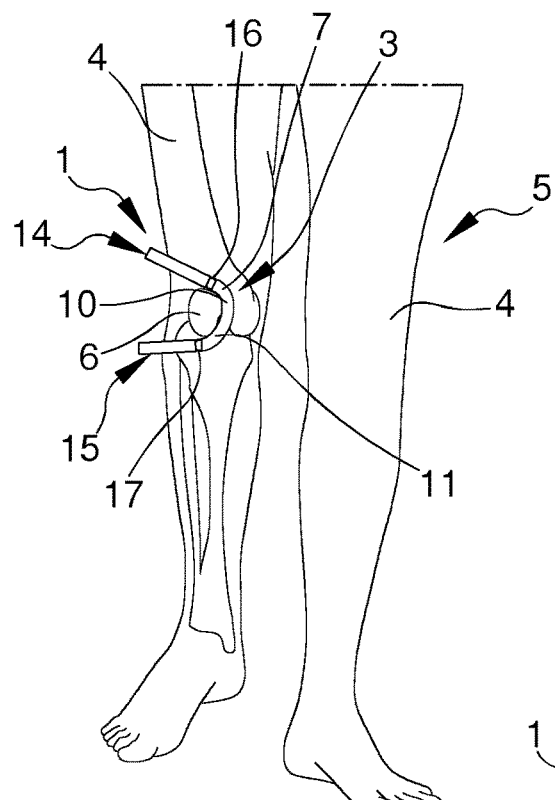
FIG. 6 is a schematic representation of the device according to the invention in the configuration of use.
Figure 7:
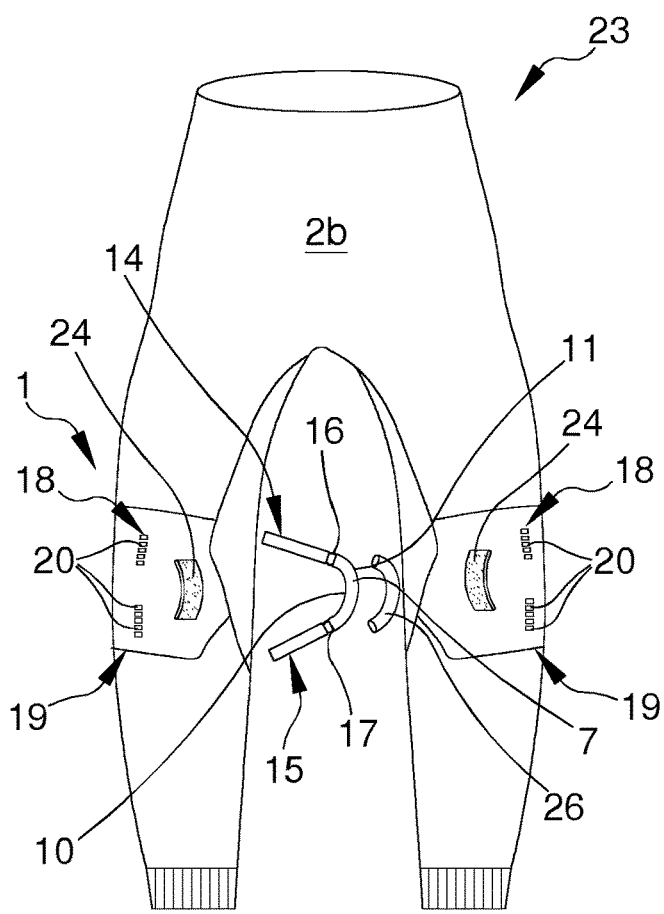
FIG. 7 is a front view of the kit according to the invention.
Figure 8:
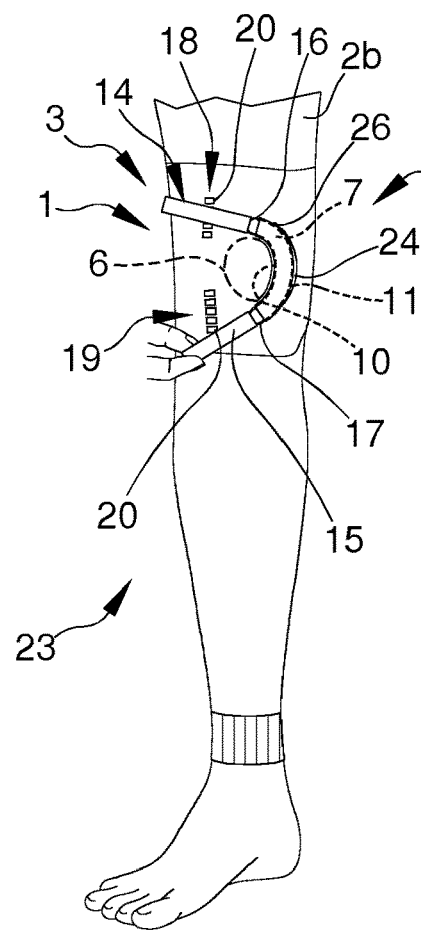
FIG. 8 is a schematic representation of the kit according to the invention in the configuration of use.

With reference to the particular embodiment shown in FIGS. 1-3, the band element 2a, in extended configuration, has four two-by-two parallel and opposite sides. In particular, the parallel sides have a semi-circular shaped portion and are adapted to overlap when the band element 2a is wrapped around the patellar portion 3.

Each semi-circular shaped portion, when arranged adjacent to each other, defines a housing seat 25 of the patella 6.

The closing means are of the mechanical type, such as e.g. Velcro.

Nevertheless, alternative embodiments cannot be ruled out, wherein the support means 2a, 2b have a reticular conformation adapted to cushion the impacts suffered by the patient 5 and to return the accumulated kinetic energy returning it to the joints in such a way as to support the latter during the movement of same.

Furthermore, it cannot be ruled out that the support means 2a, 2b are of the type of a ribbon-like element made of plasticized material and having at least one adhesive face.

In other words, the aforementioned ribbon-like element is of the type of a commonly used patch, or alternatively a taping patch.

Advantageously, the band element 2a is made of a breathable elastic material.

The device 1 comprises a sustaining element 7 of elongated shape, having a first extremity 8 and a second extremity 9 opposite to each other.

Usefully, the sustaining element 7 is made in a single monolithic body.

Moreover, the sustaining element 7 is associated with the support means 2a, 2b and positionable laterally to the patella 6 of the patient 5.

It is worth specifying that the device 1 is manufactured with the sustaining element 7 locked together with the support means 2a, 2b.

More in detail, with reference to the particular embodiment shown in the figures, the sustaining element 7 is associated on top of the support means 2a, 2b.

Nevertheless, alternative embodiments cannot be ruled out wherein the sustaining element 7 is positioned below the support means 2a, 2b. In other words, it cannot be ruled out that the sustaining element 7 be positioned in direct contact with the patella 6.

In this specific case, the sustaining element 7 comprises a first concave face 10 and a second convex face 11 opposite to the first face 10 and in which the first face 10 surrounds at least partly the patella 6.

In other words, the sustaining element 7 has a substantially C-shaped configuration and laterally surrounds the patella 6.

It is worth specifying that in the present discussion the term "laterally" refers to a configuration of use of the device 1.

The sustaining element 7 adheres to the patella 6 without leaving gaps between them; this means that the sustaining element 7 has an anatomical conformation with a profile which is substantially complementary to the lateral features of the patella 6 which enables it to fully adhere to the latter.

Furthermore, the device 1 comprises at least one housing element 26 of the sustaining element 7.

Preferably, the housing element 26 is of the type of a hollow tubular element.

The tubular element 26 is associated with the support means 2a, 2b by interposition of fastening elements of the type of Velcro or the like.

Alternative embodiments, furthermore, cannot be ruled out wherein the tubular element 26 is manufactured together with the sustaining element 7 and therefore associated with the support means 2a, 2b in an irremovable way.

In this regard it is worth specifying that the sustaining element 7 comprises transpiration means 12 adapted to allow the passage of air between the first face 10 and the second face 11.

Preferably, the transpiration means 12 comprise a plurality of through ventilation ducts 12 made on the sustaining element 7.

The ventilation ducts 12 are adapted to allow the continuous passage of air and, therefore, a homogeneous thermoregulation of the joint tissues below the device 1.

Alternatively, the transpiration means 12 comprise at least one honeycomb structure associated with the sustaining element 7.

In this case, the transpiration means 12 are locked together with the sustaining element 7; in other words, the sustaining element 7 includes the honeycomb-shaped portion.

In addition to this is the fact that the device 1 comprises a contact edge 13 associated with the first face 10 which, in the predefined position, abuts the patella 6 of the patient 5.

The contact edge 13 is preferably made of flexible material adapted to increase the wearing comfort of the device 1.

Furthermore, the device 1 comprises a first traction element 14 and a second traction element 15 associated with the first extremity 8 and with the second extremity 9 respectively.

With reference to the first embodiment shown in FIG. 1, the traction elements 14, 15 comprise at least two traction bands $14_I$, $14_{II}$, $15_I$, $15_{II}$ intertwined with each other.

In detail, such traction bands $14_I$, $14_{II}$, $15_I$, $15_{II}$ are made at least partly of extensible material; this means that, when subjected to tensile stress, they are subjected to an elastic deformation which is proportionate to the applied force.

The extensibility of the traction bands $14_I$, $14_{II}$, $15_I$, $15_{II}$ allows the neuromuscular stimulation of the muscle bands surrounding the patella 6.

As can be seen in the illustrations, the traction bands $14_I$, $14_{II}$, $15_I$, $15_{II}$ are intertwined with each other to define more or less slack weaves according to the user's needs.

In other words, the traction bands $14_I$, $14_{II}$, $15_I$, $15_{II}$ are intertwined with each other to form eyelets with decreasing diameters.

Alternatively, the traction bands $14_I$, $14_{II}$, $15_I$, $15_{II}$ are intertwined with each other to form eyelets with increasing diameters.

The possibility of varying the degree of intertwining of the traction bands $14_I$, $14_{II}$, $15_I$, $15_{II}$ permits considerably reducing the muscular stress linked to the pressure exerted by the traction bands themselves on the joints below the device 1.

Similarly, in the second embodiment shown in FIG. 3, the traction elements 14, 15 have a ribbon-like conformation.

In this case too, the traction elements 14, 15, are made of extensible material which is adapted to permit the neuromuscular stimulation of the surrounding tissue.

Furthermore, alternative embodiments cannot be ruled out in which the traction elements 14, 15 have respective extensions which are adapted to surround the patellar portion 3. In other words, the aforementioned extensions are adapted to wrap the patellar portion 3 so as to surround and envelop it.

The device 1 also comprises a first directing element 16 and a second directing element 17 which are associated with the sustaining element 7 and interposed between the first extremity 8 and the first traction element 14, and between the second extremity 9 and the second traction element 15, respectively.

The first traction element 14 and the second traction element 15 are adapted to position the sustaining element 7 in a predefined position, in detail, the first directing element 16 and the second directing element 17 are adjustable depending on the predefined position.

In particular, the first directing element 16 and the second directing element 17 are connected to the sustaining element 7 to allow for a rigid type connection with the latter.

This means that the presence of the first directing element 16 and of the second directing element 17 permit the mechanical adjustment of the patellofemoral stabilization, thus increasing the amount of forces directly transmitted to it.

Advantageously, the first directing element 16 and the second directing element 17 have a substantially C-shaped conformation.

Preferably, the first directing element 16 and the second directing element 17 are of the type of an annular element.

The first directing element 16 and the second directing element 17 are associated with the sustaining element 7 by interposition of connecting means.

The connecting means comprise through holes 27 made on the first extremity 8 and on the second extremity 9 respectively, of the sustaining element 7, and are adapted to house the annular elements 16, 17.

The orientation of the annular elements 16, 17 is determined by the synergistic combination of the relative orientation of the traction elements 14, 15 and of the sustaining element 7.

It cannot also be ruled out that the tubular element 26 have two extensions, these too tubular and associated with the respective extremal portions of the tubular element 26 and adapted to house the traction elements 14, 15.

The device 1 comprises fastening means 18, 19 for fastening the traction elements 14, 15 and retain the sustaining element 7 in the predefined position.

The fastening means 18, 19 comprise a plurality of anchoring elements 20 arranged at a predefined mutual distance and associated with a portion of the support means 2a, 2b opposite to the sustaining element 7.

The anchoring elements 20 are of the type of strips of mechanically adhesive material of the type of Velcro or the like.

As can be seen in the illustrations, the anchoring elements 20 can be divided into a first group 18 and into a second group 19 arranged symmetrically with each other.

The first group 18 is adapted to fasten the first traction element 14 and, at the same time, the second group 19 is adapted to fasten the second traction element 15.

The reciprocal symmetry of the first group 18 and of the second group 19 ensures the equally symmetrical positioning of the traction elements 14, 15 and the uniform distribution of the tractions on the sustaining element 7.

The reciprocal distance between the anchoring elements 20 determines the inclination of the traction elements 14, 15 and, at the same time, the traction force exerted by the latter on the sustaining element 7.

In detail, the first traction element 14 has a first axle 21 and the second traction element has a second axle 22.

Advantageously, the axles 21, 22 are arranged transversally to each other and the angle A comprised between them determines the traction and, therefore, the predefined position.

The present invention also relates to a joint stabilization kit 23, particularly for the patellofemoral joint.

The kit 23 comprises support means 2a, 2b which, in the present case, are of the type of a pair of trousers 2b.

Advantageously, the pair of trousers 2b is made of a breathable technical material.

The kit 23 also comprises the device 1, the detailed description of which is provided in full.

The device 1 is associable with the pair of trousers 2b by interposition of retaining means 24.

The fastening means 18, 19, in the wearing configuration of the pair of trousers 2b, are positioned at the patellar portion 3 of the patient 5.

In detail, the retaining means 24 comprise a preformed housing seat, not shown in the illustrations, made on the pair of trousers 2b and adapted to house the device 1.

Alternatively, the retaining means 24 comprise mechanical adhesion means of the type of Velcro.

Before the detailed explanation of the operation of the present invention, it is underlined that, in an alternative embodiment, the support means 2a, 2b comprise an auxiliary sustaining element of reticular conformation and associated with the sustaining element 7.

The auxiliary sustaining element enables the proprioceptive activation of the muscles wrapped by the support means 2a, 2b.

The operation of the present invention is as follows.

The device 1 is associated with the patellar portion 3 and associated therein by interposition of the closing means.

The patella is housed inside the corresponding housing seat 25 with the first face 10 of the sustaining element 7 which abuts against the patella itself.

The traction elements 14, 15 are gripped by the patient 5 and associated with the fastening means 18, 19 depending on the predefined position to be obtained.

The amplitude of the angle A comprised between the first axle 21 and the second axle 22 is proportionate to the traction exerted by the traction elements 14, 15 on the sustaining element 7.

In detail, the inclination of the first traction element 14 and of the second traction element 15 is variable according to the needs of the patient 5.

In fact, the individual anchoring elements 20 are arranged at predefined angular degrees.

At the same time, the operation of the kit 23 which the present invention refers to is as follows.

The pair of trousers 2b is worn by a user, who places the retaining means 24 at the patellar portion 3.

In this case, the fastening means 18, 19, in the wearing configuration, are also positioned at the patellar portion 3 of the patient 5.

The device 1 is therefore associated with its respective retaining means 24 and arranged depending on the predefined position to be obtained by associating the traction elements 14, 15 to the fastening means 18, 19, the detailed description of which is provided in full.

It has in practice been ascertained that the described invention achieves the intended objects.

In particular, the fact is underlined that the particular solution of providing directing means placed between the traction elements and the extremities of the sustaining element makes it possible to considerably improve the adhesion of the sustaining element itself with the patient's patella.

In addition to this is the fact that the presence of anchoring means at predefined angular positions allows activating the surrounding muscles, stimulating them from a neuromuscular point of view.

Furthermore, the synergistic combination of the contact edge and of the transpiration means permits considerably reducing the friction and the sliding of the sustaining element on the patella, ensuring tissue ventilation and reducing the muscle overheating tied to the use of the device which the present invention refers to.

Moreover, the fact of providing for the presence of the first directing element and of the second directing element makes it possible to establish a rigid connection between the sustaining element and the patient's patella, increasing the amount of forces directly transmitted to the latter.

More specifically, the conformation of the sustaining element increases the congruence and therefore the adherence with the patella, greatly increasing the effectiveness of the device according to the invention.

Finally, the possibility of adjusting the traction exerted by the traction bands significantly reduces the osteoarticular stress to which the joints are subjected during the use of the device and of the kit according to the invention.

The invention claimed is:

1. A Joint stabilization device for a patellofemoral joint, the Joint stabilization device comprising:
    support means adapted to position or capable of being positionable at a patellar portion of a leg of a patient;
    at least one sustaining element of elongated shape, having a first extremity and a second extremity opposite to each other, associated with said support means and adapted to position or capable of being positionable laterally to a patella portion of said patient;
    at least one first traction element and at least one second traction element associated with said first extremity and with said second extremity, respectively; and
    at least one first directing element and at least one second directing element which are associated with said at least one sustaining element and interposed between said first extremity and said at least one first traction element and between said second extremity and said at least one second traction element respectively, wherein
    said at least one first traction element and said at least one second traction element are adapted to position said at least one sustaining element in a predefined position,
    said at least one first directing element and said at least one second directing element being adjustable,
    each of said at least one first directing element and said at least one second directing element is of an annular element, and
    the at least one first directing element and the at least one second directing element are associated with the at least one sustaining element by interposition of through holes made on the first extremity and on the second extremity respectively, of the at least one sustaining element, and said respective through holes are adapted to house the respective annular elements.

2. The Joint stabilization device according to claim 1, wherein
    said at least one first directing element and said at least one second directing element are connected to said at least one sustaining element to allow for a rigid type connection with the latter.

3. The Joint stabilization device according to claim 1, wherein
    said at least one sustaining element comprises a first concave face and a second convex face opposite to said first concave face, and
    said first concave face adapted to surround or capable of surrounding at least partly said patella portion.

4. The Joint stabilization device according to claim 3, further comprising:
    a contact edge associated with said first concave face or said second concave face which, in said predefined position, adapted to abut or capable of abutting the patella portion of the patient.

5. The Joint stabilization device according to claim 1, wherein
    said at least one first traction element and said at least one second traction element have a ribbon-like conformation.

6. The Joint stabilization device according to claim 1, wherein
    said at least one first traction element and said at least one second traction element comprise at least two traction bands intertwined with each other.

7. The Joint stabilization device according to claim 1, further comprising:
    fastening means for fastening said at least one first traction element and said at least one second traction element and retain said at least one sustaining element in said predefined position.

8. The Joint stabilization device according to claim 7, wherein
    said fastening means comprise a plurality of anchoring elements arranged at a predefined mutual distance and associated with a portion of said support means opposite to said at least one sustaining element.

9. The Joint stabilization device according to claim 1, further comprising:
    transpiration means made on said at least one sustaining element.

10. The Joint stabilization device according to claim 8, wherein
    fastening means, in a wearing configuration, are adapted to be or capable of being positioned at the patellar portion of said patient.

11. The Joint stabilization device according to claim 1, wherein
    said support means comprise a band element adapted to envelope or capable of enveloping around the patellar portion.

12. A Joint stabilization kit for the patellofemoral joint, wherein the Joint stabilization kit comprises:
    support means of the type of a pair of trousers, and at least one stabilization device according to claim 1 associable with said pair of trousers by interposition of retaining means.

13. The Joint stabilization kit according to claim 12, further comprising:
    fastening means, in a wearing configuration, are adapted to position or capable of being positioned at the patellar portion of said patient.

14. The Joint stabilization kit according to claim 13, wherein
said retaining means comprise at least a preformed housing seat made on a pair of trousers and adapted to house said Joint stabilization device.

15. The Joint stabilization kit according to claim 13, wherein
said retaining means comprise mechanical adhesion means of a type of fastener.

16. The Joint stabilization kit according to claim 12, wherein
said retaining means comprise at least a preformed housing seat made on said pair of trousers and adapted to house said Joint stabilization device.

17. The Joint stabilization kit according to claim 12, wherein
said retaining means comprise mechanical adhesion means of a type of fastener.

18. A Joint stabilization device for a patellofemoral joint, the Joint stabilization device comprising:
support means adapted to position or capable of being positionable at a patellar portion of a leg of a patient;
at least one sustaining element of elongated shape, having a first extremity and a second extremity opposite to each other, associated with said support means and adapted to position or capable of being positionable laterally to a patella of said patient;
at least one first traction element and at least one second traction element associated with said first extremity and with said second extremity, respectively; and
at least one first directing element and at least one second directing element which are associated with said at least one sustaining element and interposed between said first extremity and said at least one first traction element and between said second extremity and said at least one second traction element respectively, wherein
said at least one first traction element and said at least one second traction element are adapted to position said at least one sustaining element in a predefined position,
said at least one first directing element and said at least one second directing element being adjustable, and
said at least one first traction element and said at least one second traction element comprise at least two traction bands intertwined with each other.

* * * * *